United States Patent [19]

Miescher

[11] Patent Number: 5,047,338
[45] Date of Patent: Sep. 10, 1991

[54] POLYESTER ANTIBIOTIC PREPARATION

[75] Inventor: Guido M. Miescher, Terre Haute, Ind.

[73] Assignee: International Minerals & Chemical Corp., Northbrook, Ill.

[21] Appl. No.: 868,014

[22] Filed: May 29, 1986

[51] Int. Cl.$^5$ .................. C12P 17/16; C12P 17/18; C12N 1/38; C07D 407/00

[52] U.S. Cl. .................. 435/118; 135/119; 135/886; 135/244; 549/414

[58] Field of Search .................. 135/253.5, 118, 170, 135/886, 244, 803; 424/123; 549/414

[56] References Cited

U.S. PATENT DOCUMENTS

| | | | |
|---|---|---|---|
| 2,844,512 | 7/1958 | Eble et al. | 435/118 |
| 3,326,775 | 6/1967 | Miescher | 195/47 |
| 3,929,575 | 12/1975 | Miescher | 195/30 |
| 3,995,027 | 11/1976 | Gale et al. | 424/115 |
| 4,009,262 | 2/1977 | Boeck et al. | 424/123 |
| 4,033,823 | 7/1977 | Liu et al. | 435/118 |
| 4,035,481 | 7/1977 | Berg et al. | 424/122 |
| 4,038,384 | 7/1977 | Berg et al. | 424/122 |
| 4,085,224 | 4/1978 | Berg et al. | 424/283 |
| 4,110,435 | 8/1978 | Nakatsukasa et al. | 424/122 |
| 4,110,436 | 8/1978 | Nakatsukasa et al. | 424/122 |
| 4,137,241 | 1/1979 | Liu et al. | 260/345.7 |
| 4,141,907 | 2/1979 | Nakatsukasa et al. | 260/345.7 |
| 4,174,390 | 11/1979 | Hamill et al. | 424/117 |
| 4,174,404 | 11/1979 | Nakatsukasa et al. | 424/283 |
| 4,204,039 | 5/1980 | Nakatsukasa et al. | 435/118 |
| 4,212,942 | 7/1980 | Miyazaki et al. | 435/119 |
| 4,214,091 | 7/1980 | Oishi et al. | 549/62 |
| 4,221,724 | 9/1980 | Liu et al. | 260/345.8 |
| 4,263,427 | 4/1981 | Liu et al. | 536/1 |
| 4,266,028 | 5/1981 | Nakamura et al. | 435/118 |
| 4,283,493 | 8/1981 | Liu et al. | 435/119 |
| 4,294,925 | 10/1981 | Liu et al. | 435/84 |
| 4,395,491 | 7/1983 | Hohl et al. | 435/262 |
| 4,440,857 | 4/1984 | Seno et al. | 435/118 |

FOREIGN PATENT DOCUMENTS 0679087  2/1950  United Kingdom ............ 435/897

OTHER PUBLICATIONS

Mehrotra et al., Int. J. of Mineral Processing, vol. 1, 11 (1983), 175–201.
W. M. Stark et al., *Antimicrobial Agents and Chemotherapy*, pp. 353–358 (1967).
Stark et al., *Antimicrobial Agents and Chemotherapy*, 1967, pp. 353–358.
Ralston, A. W., *Fatty Acids and Their Derivatives*, pp. 281–289, 1948, J. Wiley and Sons.
Morrison et al., *Organic Chemistry*, pp. 1059–1061, 1980, Allyn and Bacon.

*Primary Examiner*—Douglas W. Robinson
*Assistant Examiner*—Irene Marx
*Attorney, Agent, or Firm*—Wendell Ray Guffey; Thomas L. Farquer

[57] ABSTRACT

A polyether and antibiotic material is prepared by forming discrete polyether antibiotic-containing agglomerates which are separable from an aqueous medium, by producing a polyether antibiotic through cultivation of a polyether antibiotic-producing microorganism in a generally aqueous nutrient-containing fermentation broth under conditions wherein at the end of fermentation, a lipid is present in the broth in a sufficient amount to form discrete agglomerates with polyether and antibiotic in the fermentation broth, whereupon the applomerates are separated from the broth.

21 Claims, No Drawings 5,047,338

POLYESTER ANTIBIOTIC PREPARATION

BACKGROUND OF THE INVENTION

1. Field of the Invention

The present invention relates to a polyether antibiotic-containing material and to a method for preparing same.

2. Description of the Background Art

Polyether antibiotics can be generally characterized as carboxylic acid ionophores which can be produced by culturing Streptomyces type microorganisms. These polyether antibiotics have a basic structure generally consisting essentially of the elements oxygen, hydrogen and carbon and possibly nitrogen and have a molecular weight in the range of about 300 to about 1800, most often from about 400 to about 1200. They have low solubility in water, are generally soluble in low molecular weight alcohols, ethers and ketones, and have at least one, and usually one or two, carboxylic acid groups. A generally comprehensive review of this class of antibiotics is set forth in Westley, *Adv. Appl. Microbiology*, 22:177–223 (1977). At least twenty different polyether antibiotics were known at the time the Westley article was written. Since then, additional polyether antibiotics have been discovered.

In the previously noted publication, Westley classified the known polyether antibiotics into four separate classes based on ability of the particular antibiotic to effect the transport of divalent cations and based on the chemical structure of the particular antibiotic. Using these criteria, Westley defined class 1a as those polyether antibiotics which are monovalent polyether antibiotics. In addition, the polyether antibiotics of this class have a generally linear configuration, i.e., the carboxylic portion of the polyether molecule is attached either directly or indirectly to a terminal ring structure. They generally include from about four to about six tetrahydropyran and/or -furan structures and up to six total ring structures. Included in class 1a are the polyether antibiotics monensin, laidlomycin, nigericin, grisorixin, salinomycin, narasin, lonomycin, X-206, SY-1, noboritomycins A & B, mutalomycin, and alborixin.

Class 1b of the polyether antibiotics are defined by Westley as monovalent monoglycoside polyether antibiotics. These polyether antibiotics, as the class name suggests, include a glycoside type structure, more specifically, a 2,3,6-trideoxy-4-O-methyl-D-erythrohexapyranose moiety, which is attached to the polyether molecule such that a non-linear type molecule is formed, i.e., the carboxylic portion of the polyether molecule is attached either directly or indirectly to a non-terminal ring structure or the molecule has a side chain ring structure, e.g., a 2,3,6-trideoxy-4-O-methyl-D-erythrohexapyranose moiety. Generally, the polyether antibiotics of this class contain about six or seven tetrahydropyran and/or -furan structures. Included within class 1b are the polyether antibiotics septamycin, dianemycin, A-204, lenoremycin, carriomycin and etheromycin.

Class 2a as defined by Westley is directed to divalent polyether antibiotics. These antibiotics have a generally linear configuration, may contain from about two to about three tetrahydropyran and/or -furan structures, up to about three total ring structures and no nitrogen atoms. Included within class 2a are the antibiotics lasalocid and lysocellin.

Westley's class 2b of polyether antibiotics is directed to divalent pyrrole ethers and thus, in contrast to the antibiotics of the other classes, the class 2b antibiotics contain one or more nitrogen atoms. Included within class 2b are the polyether antibiotics X-14547, and A-23187 also known as calcimycin.

Polyether antibiotics are generally produced by fermenting a nutrient-containing liquid fermentation medium or broth inoculated with a microorganism capable of producing the desired antibiotic. Suitable liquid fermentation media are generally aqueous dispersions containing sources of assimilable nitrogen and carbon as is known in the art. The fermentation media can also contain a variety of optional ingredients, if desired, such as for example, pH adjustment agents, buffers, trace minerals, antifoam agents, and the like.

Known methods for recovering polyether antibiotics from fermentation broths generally involve complicated and expensive multi-stage solvent extractions and related filtration, chromatography, concentration, and crystallization operations. For example, the procedure to isolate and purify lysocellin first described by Ebata et al. used acetone, n-butanol and methanol (Ebata et al., *J. Antibiotics*, 28:118–121 (1975)). U.S. Pat. No. 4,033,823 describes an extraction process involving ethyl acetate, acetonitrile, hexane and methanol for recovering lysocellin. Commonly owned U.S. Pat. No. 4,478,935 describes various purified manganese-containing antibiotic complexes extracted from the dried biomass using suitable organic solvents followed by crystallization or precipitation of the complexes. All of these processes follow a rather standard approach in which fermentation broths are subjected to organic solvent extraction to recover the polyether antibiotics. The isolation and purification of polyether antibiotics using extraction methods have been extensively reviewed in Hamill et al., "Polyether Antibiotics" pp. 479–520, *J. Chromatogr. Lib.*, Vol. 15. Antibiotics: Isolation, Separation, and Purification, ed. by Weinstein, M. J. and Wagman, G. H. (1978).

There remains a need in the art for a method for preparing polyether antibiotic material without the need for complicated and expensive multi-stage solvent extractions and related filtration, chromatography, concentration and crystallization operations and the like.

SUMMARY OF THE INVENTION

In accordance with the present invention, a method for preparing a polyether antibiotic material comprises forming discrete polyether antibiotic-containing agglomerates which are separable from an aqueous medium by producing a polyether antibiotic through cultivation of a polyether antibiotic-producing microorganism in a generally aqueous fermentation broth under conditions wherein at the end of fermentation, a physiologically acceptable lipid is present in the broth in a sufficient amount to form discrete agglomerates of said lipid with polyether antibiotic in the fermentation broth, which agglomerates are separated from the fermentation broth.

DETAILED DESCRIPTION OF THE PREFERRED EMBODIMENTS

Polyether antibiotic material is produced according to one aspect of this invention using a polyether antibiotic-producing microorganism which secretes a lipophilic polyether antibiotic into an aqueous medium. According to one embodiment, a polyether antibiotic-producing microorganism, such as a lysocellin-producing strain of *Streptomyces cacaoi var. asoensis* is cultivated in a generally aqueous fermentation broth (sometimes referred to herein as culture medium or nutrient medium). Although the invention is specifically described herein with respect to the preparation of a lysocellin material, it is to be understood that the invention is also applicable to other polyether antibiotics.

The agglomerates of the invention are formed between polyether antibiotic material and a physiologically acceptable lipid. The agglomerates (or aggregates) are formed by producing a polyether antibiotic through cultivation of a polyether antibiotic-producing microorganism in a generally aqueous fermentation broth under conditions wherein at the end of fermentation sufficient lipid is present in the fermentation broth to form discrete agglomerates with polyether antibiotic in the fermentation broth. As fermentation proceeds, polyether antibiotic accumulates in the broth, and it has been found that if a lipid is present in the medium, the polyether antibiotic is attracted to the lipid due to the lipophilic nature and water insolubility of the polyether antibiotic. If, at the end of fermentation, sufficient lipid is present in the fermentation broth, agglomerates in the form of separable paste or pellets will form between the lipid and polyether antibiotic.

For growth of the microorganism and production of polyether antibiotic, the fermentation broth contains assimilable sources of carbon and nitrogen, and may contain trace elements and other optional ingredients, as is known in the art. In accordance with one embodiment, the lipid for forming agglomerates is an assimilable source of carbon for the microorganism.

Examples of lipids which are suitable for use according to this invention include glyceride fats and oils, free fatty acids, and phospholipids such as lecithin. If during the fermentation, a principal carbon source other than a lipid is used, or the carbon source is depleted at the end of fermentation, it may be necessary to add sufficient lipid at or near the end of fermentation in order to form the desired agglomerates. In one embodiment, however, at least a portion of the principal carbon source during fermentation comprises the lipid.

An assimilable source of nitrogen is also provided in the culture medium. Suitable sources of nitrogen include yeast, yeast-derived products, enzyme-hydrolyzed caseine, peptones, cornmeal, soybean meal, cottonseed meal, amino acids such as glutamic acid, and the like.

Nutrient inorganic salts can also be incorporated in the culture medium such as soluble salts capable of yielding sodium, magnesium, calcium, ammonium, chloride, carbonate, sulfate, nitrate, and like ions. Essential trace elements necessary for the growth and development of the microorganism should also be included in the culture medium. Such trace elements commonly occur as impurities in other constituents of the medium in amounts sufficient to meet the growth requirements of the organism.

Polyether antibiotics are produced by growing the polyether antibiotic-producing microorganism in an aerated, agitated, submerged culture with the pH of the broth adjusted to about neutral, i.e., from about 6.5 to about 7.5. Fermentation can generally be carried out at slightly elevated temperatures, e.g., between about 25° C. and 35° C. Incubation of the broth can be carried out for a period of several days, e.g., from about 4 to 12 days or longer if it is economically advantageous to do so.

It may be necessary to add small amounts (i.e., 0.2 ml/l) of an anti-foam agent such as polypropylene glycol to large-scale fermentation media if foaming becomes a problem. Excessive foaming may occur, for example, when fatty acids are added initially to the fermentation broth as the principal carbon source.

In one embodiment, the lipid for forming agglomerates with polyether antibiotic is comprised of glycerides. Suitable glycerides include soybean oil, safflower oil, cottonseed oil, sesame oil, olive oil, rape oil, peanut oil, corn oil, sunflower oil and like vegetable oils, cod oil and like fish oils, and lard and like animal-fat-and-oils. Vegetable oils are a preferred glyceride source, with soybean oil being particularly preferred.

A respective ratio by weight of polyether antibiotic to glycerides in the fermentation broth of about 1:2 or greater will generally produce separable agglomerates in the form of semi-solid paste or pellets. If the ratio by weight of polyether antibiotic to glycerides is less than about 1:2, the resulting oily mass containing accrued polyether antibiotic tends to clog screens and is difficult to separate from the balance of the fermentation broth.

According to one embodiment, the respective ratio by weight of polyether antibiotic to glycerides in the fermentation broth at the end of fermentation is from about 1:2 to about 3:1. Generally, if the ratio of polyether antibiotic to glycerides is greater than about 3:1 by weight, separable agglomerates will form between the available glycerides and polyether antibiotic, but non-aggregated polyether antibiotic will remain in the fermentation broth due to an insufficient amount of glycerides, making recovery of the non-aggregated antibiotic material difficult.

If at the end of fermentation the respective ratio by weight of polyether antibiotic to glycerides in the fermentation broth is from about 1:1 to about 2:1, the resulting agglomerates take the form of solid or semi-solid pellets or beads ranging in size from about 3 mm to about 10 mm which may easily be separated from the broth using a coarse screen (e.g., U.S. standard series No. 35). If desired, the separated agglomerates can be washed with water to further cleanse the material.

According to one embodiment, the fermentation broth contains as a principal carbon source glycerides or a mixture of free fatty acids and glycerides. The free fatty acids which may be used according to the present invention include saturated fatty acids such as lauric acid, myristic acid, palmitic acid, stearic acid, arachidic acid, lignoceric acid and the like, and unsaturated fatty acids such as palmitoleic acid, oleic acid, linoleic acid, linolenic acid, arachidonic acid and the like. Unsaturated fatty acids are preferable for use according to the present invention, with oleic acid being most preferred.

In a particularly preferred embodiment, the fermentation broth contains as a principal carbon source a mixture of free fatty acids and glycerides, most preferably a mixture of oleic acid and soybean oil. According to this embodiment, the respective ratio by weight of oleic acid to soybean oil during at least a portion of fermentation is from about 4:1 to about 1:1.

Free fatty acids, such as oleic acid, are much more quickly metabolized during fermentation as compared to glyceride oils, but are generally quite toxic to microorganisms except at low concentrations. Free fatty acids can thus advantageously be used to obtain higher antibiotic yields or titers by continuously feeding low concentrations of free fatty acids to the broth during fermentation at about a rate at which the free fatty acids are metabolized. If free fatty acids are used alone during fermentation as principal carbon source and are depleted at the end of fermentation, accruing crystals of polyether antibiotic are freely suspended in the fermentation broth and do not form agglomerates. Addition of at least a small amount of glycerides with free fatty acids during fermentation, which is preferably fed on a continuous basis to the on-going fermentation, can result in sufficient triglycerides being present in the broth to facilitate the formation of agglomerates.

According to one embodiment, growth of a lysocellin-producing strain of the genus Streptomyces is established in a generally aqueous fermentation broth initially containing as a principal carbon source from about 1% to about 10% (preferably 1-5%, more preferably 2-3%) by weight glycerides such as soybean oil. After growth has been established and the pH of the broth begins to rise (e.g., after about 15-20 hours of fermentation), free fatty acids such as oleic acid is fed to the fermentation broth to achieve and maintain a free fatty acids concentration in the fermentation broth of about 0.1% by weight or more (preferably from about 0.1% to about 0.4% by weight) during fermentation which a lysocellin titer in the broth in excess of about 20 gm/l is achieved.

Advantageously, the free fatty acids are fed to the broth in combination with glycerides during fermentation. For example, according to this embodiment, oleic acid and soybean oil are fed in a respective ratio by weight of from about 4:1 to about 1:1 to the fermentation broth to achieve and maintain an oleic acid concentration in the fermentation broth of from about 0.1% to about 0.4% by weight during fermentation. The free fatty acids and glycerides are fed to the broth during fermentation until the desired concentration of lysocellin in the fermentation broth is achieved, e.g., generally in about 10-12 days.

At the end of fermentation, e.g., during the last 24 hours of fermentation, a respective ratio by weight of lysocellin to glycerides in the broth of about 1:2 or greater is achieved to form glyceride/lysocellin agglomerates which are separable from the broth. If excess glycerides are present in the broth during the final stages of fermentation, glyceride addition to the broth is terminated until sufficient glycerides have been metabolized to achieve the desired glyceride/lysocellin ratio. If insufficient glycerides are present in the broth towards the end of fermentation, additional glycerides may be added to the fermentation broth to achieve the desired glyceride/lysocellin ratio. The resulting glyceride/lysocellin agglomerates can be separated from the balance of the fermentation broth by screening as noted above.

Agglomerates of the present invention are particularly useful as providing means for obtaining very pure polyether antibiotic material in a relatively inexpensive manner. For recovery of the polyether antibiotic from the agglomerates, the agglomerates are mixed with water several times to remove residual aqueous broth, cell debris, and/or mycelia. The clean agglomerates are then added to an aqueous solution with base (e.g., 2% NaOH (aq) or KOH (aq)) to achieve and maintain a pH of about 10 or higher, in order to form an acid salt of the lipid and liberate the polyether antibiotic as an insoluble acid salt. At the same time, free acid or other salts of the polyether antibiotic can be converted to the desired salt form of the product, e.g., sodium salt with NaOH, potassium salt with KOH. Preferably, the aqueous medium has a weight of from about 5 to about 20 times that of said agglomerates, and the pH is raised to about 12-14 by NaOH addition. In order to facilitate rapid formation of acid salts of the lipids present in the agglomerates, the solution containing agglomerates and NaOH is advantageously agitated for from about 1 to about 5 hours to substantially completely form said salts of the lipids to liberate the insoluble polyether antibiotic salts.

The insoluble polyether antibiotic material then is isolated, e.g., by centrifugation or filtration, from the aqueous soap solution. The wet solids are reslurried several times into water to further remove residual base and lipid salts. The solution can be dewatered by solid-liquid separation, e.g., centrifugation or filtration, to isolate lysocellin solids, which are then dried in a vacuum oven or tumble drier to obtain the final product. This process has been utilized to obtain lysocellin purities for dried solids obtained directly from the soap solution in the range of from about 70-99%. Optionally, additional hexane washes can be utilized to improve the purities to 95-99% without significantly decreasing recoveries since the solids from the NaOH solution generally contain more than 90% of the desired sodium salt of lysocellin which is essentially insoluble in hexane. Additional sodium conversion is possible for the crude lysocellin crystals when mixed with caustic in methanol. The crude lysocellin crystals can also be dissolved into methanol, ethanol and the like, to filter off the insoluble impurities, e.g., mycelia and cell debris.

By controlling the amount of lipid in the broth at the end of fermentation, it is possible to steer the fermentation either towards the formation of agglomerates or avoiding agglomerate formation. For example, the microorganism can be grown using assimilable lipid as the principal carbon source, and lipid introduction terminated near the end of fermentation to substantially deplete the lipid. This allows the whole fermentation broth to be harvested and spray- or drum-dried to produce an economical biomass product containing polyether antibiotic.

The present invention can be utilized to prepare a polyether antibiotic material of high purity without the need for complicated and expensive multi-stage solvent extractions and related filtration, chromatography, concentration and crystallization operations.

The invention is further illustrated by the following examples which is not intended to be limiting.

EXAMPLE I

Seed Development

Capsules of seed culture of a lysocellin-producing strain of *S. cacaoi var. asoensin* containing 1 ml of culture in glycerol were stored at −80° C. The content of one capsule was added to 80 ml first stage inoculum medium in a 500 ml Erlenmeyer flask. The medium contained (in wt. %) glycerol (2%), Bacto Peptone (1%), Bacto Meat Extract (1%), and tap water to volume. The flask was incubated on a rotary action shaker (~350 rpm) at 28°-30° C. for 48 hours (until satisfactory growth was established), and this seed was used immediately to inoculate the second stage inoculum as follows.

2.5 Percent of the first stage inoculum was added to 100 ml second stage inoculum medium in each of several 500 ml Erlenmeyer flasks. The medium contained (by wt. %) soybean oil (2.5%), soybean flour (2.5%), $KH_2PO_4$ (0.15%), $K_2HPO_4$ (0.15%), and the trace elements $FeSO_4 \cdot 7H_2O$ (5 ppm), $MnSO_4 \cdot H_2O$ (1.5 ppm), $CoCl_2 \cdot 6H_2O$ (0.5 ppm), and distilled water. The flasks were incubated on rotary action shakers (~350 rpm) at 28°–30° C. for about 24 hours. The second stage inoculum was transferred immediately from shaker to fermenter.

source concentration in the medium in the range between 0.1 and 0.4%.

The fermentation results are shown in Table 1 below, which indicates the feed mixture used, final lysocellin titers and agglomerate formation.

TABLE 1

Final Lysocellin Titers in Fermentation Using Various Feeding Combinations of Oleic Acid and Soy Oil

| Batch No. | Variation Medium | Final Lysocellin Titer g/l | Initial Soy Oil in Medium % | Feed Mixture Soy Oil % | Feed Mixture Oleic Acid % | Agglomerate Separation by Screening- % Lysocellin in the Form of: Agglomerates | Filtrate |
|---|---|---|---|---|---|---|---|
| 100% Oleic Acid Fed | | | | | | | |
| 1 | a | 35 | 3 | 0 | 100 | very few agglomerates | |
| 2 | b | 29 | 3 | 0 | 100 | very few agglomerates | |
| 20% Soybean Oil/80% Oleic Acid Fed | | | | | | | |
| 3 | none | 29 | 3 | 20 | 80 | 80 | 20 |
| 4 | none | 26 | 3 | 20 | 80 | 91.5 | 8.5 |
| 5 | c | 36 | 3 | 20 | 80 | 88.5 | 11.5 |
| 30% Soybean Oil/70% Oleic Acid Fed | | | | | | | |
| 6 | c | 29 | 3 | 30 | 70 | 91 | 9 |
| 40% Soybean Oil/60% Oleic Acid Fed | | | | | | | |
| 7 | none | 32 | 3 | 40 | 60 | 94.5 | 5.5 |
| 8 | none | 36 | 3 | 40 | 60 | 92 | 8 |
| 60% Soybean Oil/40% Oleic Acid Fed | | | | | | | |
| 9 | none | 19 | 3 | 60 | 40 | oily mush-not screenable | |
| 100% Soybean Oil Used | | | | | | | |
| 10 | a | 19 | 7.5 | (no feed) | | 78 | 22 |
| 11 | a | 19 | 7.5 | (no feed) | | small oily beads-not screenable | | a Medium contains soy flour (4.5%), soy oil (according to table), $KH_2PO_4$ (.1%), $K_2HPO_4$ (.2%), $CaCO_3$ (.4%), $FeSO_4 \cdot 7H_2O$ (50 ppm), and $CoCl_2 \cdot 6H_2O$ (2 ppm), with tap water.
b Medium contains soy flour (4.5%), soy oil (according to table), $KH_2PO_4$ (.05%), $K_2HPO_4$ (.15%), $CoCl_2 \cdot 6H_2O$ (1 ppm), with tap water.
c Only variation from "standard" medium described above is 0.4% soy flour.

EXAMPLE II

Main Fermentation

In separate fermentations, 200 milliliters from 2 flasks of the second stage inoculum were used (~2% wt.) to inoculate a 20-liter sterilized fermenter containing (by wt. %) as "standard" principal medium soybean flour (4.5%), soybean oil (3%), $KH^2PO^4$ (0.05%), $K^2HPO^4$ (0.15%), and $CoCl_2 \cdot 6H_2O$ (1 ppm). Hodag K-67 antifoam (about 0.1%) and tap water to about a 10 liter volume. The pH of the inoculated medium was about neutral and did not require any further pH adjustment.

The physical parameters for fermentations using a New Brunswick fermenter were as follows:

| Medium, volume | 10,000 ml | |
|---|---|---|
| Air | 10 l/min | (5 l/min during first 16 hr) |
| PSI g | 4 | |
| Agitation | 2 impellors, 10.8 cm diam. | |
| RPM | 650 | |
| Temperature | 29–30° C. | |

Oleic acid alone, mixtures of oleic acid and soybean oil or soybean oil alone was fed into the various fermentation broths when the pH of the fermentations began to rise, indicating the development stage of the fermentation (about 15–20 h after inoculation). The feed rate was about 0.5% (wt.) per day to maintain an oleic carbon The above table demonstrates aggregate formation obtained according to the invention.

What is claimed is:

1. A method for producing a polyether antibiotic material comprising:
   (a) forming discrete polyether antibiotic-containing agglomerates which are separable from an aqueous medium by producing a polyether antibiotic through cultivation of a polyether antibiotic-producing microorganism in a generally aqueous nutrient-containing fermentation broth under conditions wherein at the end of fermentation, a lipid is present in the broth in a sufficient amount to form discrete agglomerates with polyether antibiotic in the fermentation broth, which agglomerates are separable from the fermentation broth; and
   (b) separating the agglomerates from the broth.

2. The method of claim 1 wherein said lipid is an assimilable lipid comprised of glycerides, fatty acids or mixtures thereof.

3. The method of claim 2 wherein at the end of fermentation the respective ratio by weight of polyether antibiotic to glycerides in the fermentation broth is about 1:2 or greater.

4. The method of claim 2 wherein at the end of fermentation the respective ratio by weight of polyether antibiotic to glycerides in the fermentation broth is from about 1:2 to about 3:1.

5. The method of claim 4 wherein said ratio is from about 1:1 to about 2:1.

6. The method of claim 5 wherein the polyether antibiotic is lysocellin.

7. The method of claim 2 wherein the fermentation broth contains as a principal carbon source glycerides, free fatty acids or a mixture thereof.

8. The method of claim 2 wherein the fermentation broth contains as a principal carbon source a mixture of free fatty acids and glycerides.

9. The method of claim 8 wherein the polyether antibiotic is lysocellin.

10. The method of claim 2 wherein said glycerides are present in soybean oil, and wherein the fermentation broth contains as a principal carbon source a mixture of oleic acid and soybean oil.

11. The method of claim 10 wherein the respective ratio by weight of oleic acid to soybean oil during at least a portion of fermentation is from about 4:1 to about 1:1.

12. The method of claim 11 wherein the polyether antibiotic is lysocellin.

13. The method of claim 12 wherein at the end of fermentation the respective ratio by weight of polyether antibiotic to glycerides in the fermentation broth is about 1:2 or greater.

14. The method of claim 12 wherein at the end of the fermentation the respective ratio by weight of polyether antibiotic to glycerides in the fermentation broth is from about 1:1 to about 2:1.

15. A method for producing glyceride/lysocellin agglomerates comprising:
(a) establishing growth of a lysocellin-producing strain of the genus Streptomyces in a generally aqueous fermentation broth containing glycerides as a principal carbon source in an amount sufficient to establish growth of the microorganism in the broth, and then
(b) feeding free fatty acids to the fermentation broth to achieve and maintain a free fatty acids concentration in the fermentation broth of about 0.1% by weight or greater, but less than an amount which is toxic to the microorganism, wherein said free fatty acids are fed to the broth at about a rate at which they are consumed, to achieve a lysocellin titer in the broth in excess of about 20 gm/l, while achieving a respective ratio by weight of lysocellin to glycerides in the broth of about 1:2 or greater to form discrete glyceride/lysocellin agglomerates which are separable from the broth; and
(c) separating the agglomerates from the broth.

16. The method of claim 15 wherein the glycerides comprise soybean oil and the fermentation broth in step (a) contains from about 2% to about 3% by weight soybean oil; and wherein said free fatty acids comprise oleic acid and in step (b) oleic acid and soybean oil are fed in a respective ratio by weight of from about 4:1 to about 1:1 to the fermentation broth to achieve and maintain an oleic acid concentration in the fermentation broth of from about 0.1% to about 0.4% by weight during fermentation.

17. The method of claim 16 wherein the ratio of step (b) is from about 1:2 to about 3:1.

18. The method of claim 17 wherein the ratio of step (b) is from about 1:1 to about 2:1.

19. Agglomerates of lysocellin and triglycerides which are separable from an aqueous medium by screening.

20. The agglomerates of claim 19 wherein the glycerides comprise soybean oil and the ratio by weight of lysocellin to soybean oil respectively in the agglomerates is from about 1:2 to about 3:1.

21. The agglomerates of claim 20 wherein the respective ratio is from about 1:1 to about 2:1.

* * * * *

UNITED STATES PATENT AND TRADEMARK OFFICE
CERTIFICATE OF CORRECTION

PATENT NO. : 5,047,338

DATED : September 10, 1991

INVENTOR(S) : Guido M. Miescher

It is certified that error appears in the above-identified patent and that said Letters Patent is hereby corrected as shown below: Title page:

In the Title, "Polyester" should read --Polyether--

In the Abstract, Line 1, delete "and"
Line 9, delete "and"
Lines 10-11, "applomerates" should read
--agglomerates--

Signed and Sealed this

Twelfth Day of January, 1993

Attest:

DOUGLAS B. COMER

*Attesting Officer*   *Acting Commissioner of Patents and Trademarks*